US006733476B2

(12) United States Patent
Christenson et al.

(10) Patent No.: US 6,733,476 B2
(45) Date of Patent: May 11, 2004

(54) IMPLANTABLE DRUG DELIVERY DEVICE WITH PERISTALTIC PUMP HAVING A BOBBIN ROLLER ASSEMBLY

(75) Inventors: Steven R. Christenson, Coon Rapids, MN (US); James Randall, Coon Rapids, MN (US); Micheal Thomas Hegland, Mounds View, MN (US); James M. Haase, Blaine, MN (US); Mark S. Lent, Brooklyn Park, MN (US); William H. Monsen, Rochester, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/835,208

(22) Filed: Apr. 13, 2001

(65) Prior Publication Data

US 2002/0173755 A1 Nov. 21, 2002

(51) Int. Cl.⁷ .................................................. A61M 1/00

(52) U.S. Cl. .................. 604/151; 417/477.1; 417/477.7

(58) Field of Search ................................. 604/151, 153, 604/131; 417/477.3, 477.7, 477.1, 474, 476, 423.6

(56) References Cited

U.S. PATENT DOCUMENTS

| | | | |
|---|---|---|---|
| 2,804,023 A | | 8/1957 | Lee |
| 3,644,068 A | | 2/1972 | Lepak |
| 3,822,948 A | | 7/1974 | Handl |
| 3,885,894 A | | 5/1975 | Sikes |
| 3,927,955 A | | 12/1975 | Spinosa et al. |
| 3,960,466 A | | 6/1976 | Taylor |
| 3,963,023 A | | 6/1976 | Hankinson |
| 4,013,074 A | * | 3/1977 | Siposs ...................... 222/386.5 |
| 4,363,609 A | * | 12/1982 | Cosentino et al. ....... 417/477.5 |
| 4,564,342 A | | 1/1986 | Weber et al. |

(List continued on next page.)

FOREIGN PATENT DOCUMENTS

| | | |
|---|---|---|
| DE | 24 52 771 A1 | 5/1976 |
| DE | 101 19 391 | 11/2001 |
| EP | 0 174 535 A1 | 3/1986 |
| EP | 0 239 255 | 9/1987 |
| EP | 0 320 441 | 6/1989 |
| EP | 0 344 640 A1 | 12/1989 |
| EP | 0 547 550 A1 | 6/1993 |
| FR | 2 021 524 | 7/1970 |
| FR | 2 644 853 A1 | 9/1990 |
| FR | 2 719 873 A1 | 11/1995 |
| FR | 2 808 203 | 11/2001 |

OTHER PUBLICATIONS

U.S. patent application Ser. No. 09/834,874, entitled "Implantable Drug Delivery Device with Peristaltic Pump Having a Retracting Roller", filed Apr. 13, 2001, (P–9175.00).
U.S. patent application Ser. No. 09/561,154, entitled, "Implantable Drug Infusion Device with Peristaltic Pump using Tube Guide", filed Apr. 28, 2000. (P–9176.00).
U.S. patent application Ser. No. 09/561,583 entitled "Spring Loaded Implantable Drug Infusion Device", filed Apr. 28, 2000. (P–8901.00).

Primary Examiner—Edward K. Look
Assistant Examiner—John K. Fristoe, Jr.
(74) Attorney, Agent, or Firm—Banner & Witcoff, Ltd.

(57) ABSTRACT

An implantable drug infusion device includes a pump tube for holding a liquid to be pumped. A race is configured to support the pump tube. A roller assembly is configured to compress the tube against the race at one or more points along the path, and the roller assembly includes at least one roller. A drive assembly drives the roller assembly relative to the tube along the path so as to move the liquid through the tube. At least two biasing members are operably connected to the roller to bias the roller against the tube, the two biasing members forming an angle.

40 Claims, 14 Drawing Sheets

U.S. PATENT DOCUMENTS

| | | | | |
|---|---|---|---|---|
| 4,576,556 A | * | 3/1986 | Thompson | 417/477.12 |
| 4,692,147 A | | 9/1987 | Duggan | |
| 5,083,908 A | * | 1/1992 | Gagnebin et al. | 417/477.1 |
| 5,125,801 A | | 6/1992 | Nabity et al. | |
| 5,215,450 A | * | 6/1993 | Tamari | 138/119 |
| 5,405,614 A | * | 4/1995 | D'Angelo et al. | 424/449 |
| 5,576,503 A | | 11/1996 | Nabity et al. | |
| 5,741,125 A | | 4/1998 | Neftel et al. | |
| 5,752,930 A | | 5/1998 | Rise et al. | |
| 5,840,069 A | | 11/1998 | Robinson | |
| 5,915,932 A | | 6/1999 | Nabity et al. | |
| 6,036,459 A | * | 3/2000 | Robinson | 417/477.11 |
| 6,041,709 A | * | 3/2000 | Wells et al. | 101/366 |
| 6,195,887 B1 | | 3/2001 | Danby et al. | |

* cited by examiner

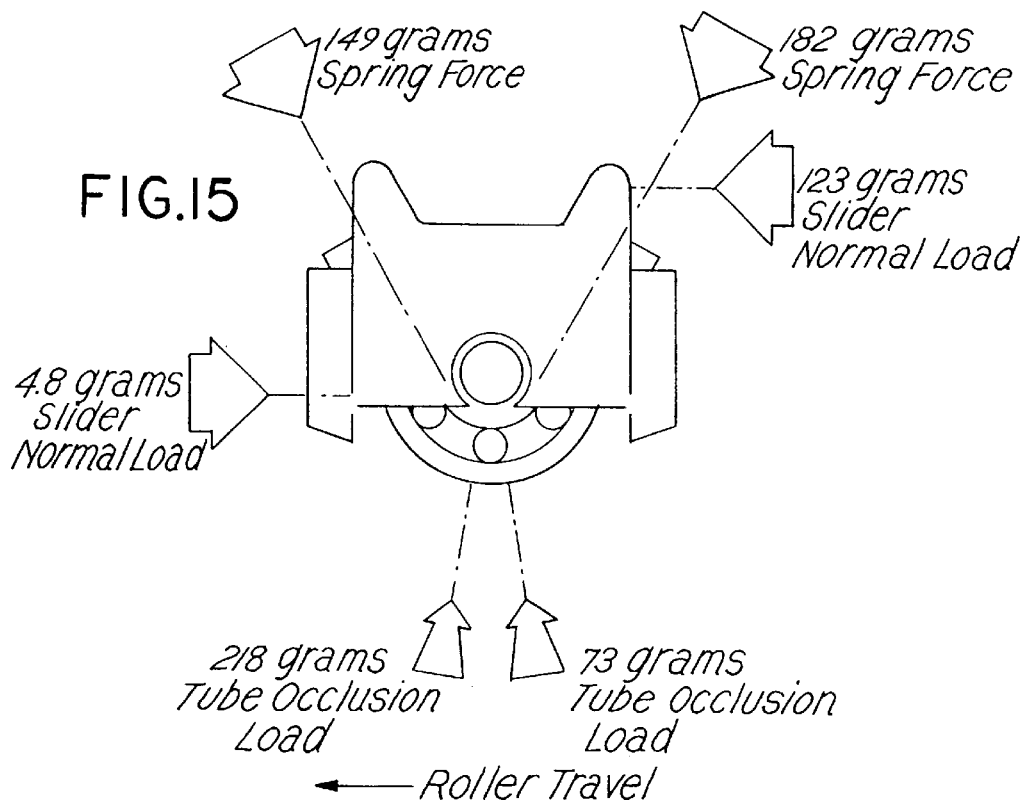
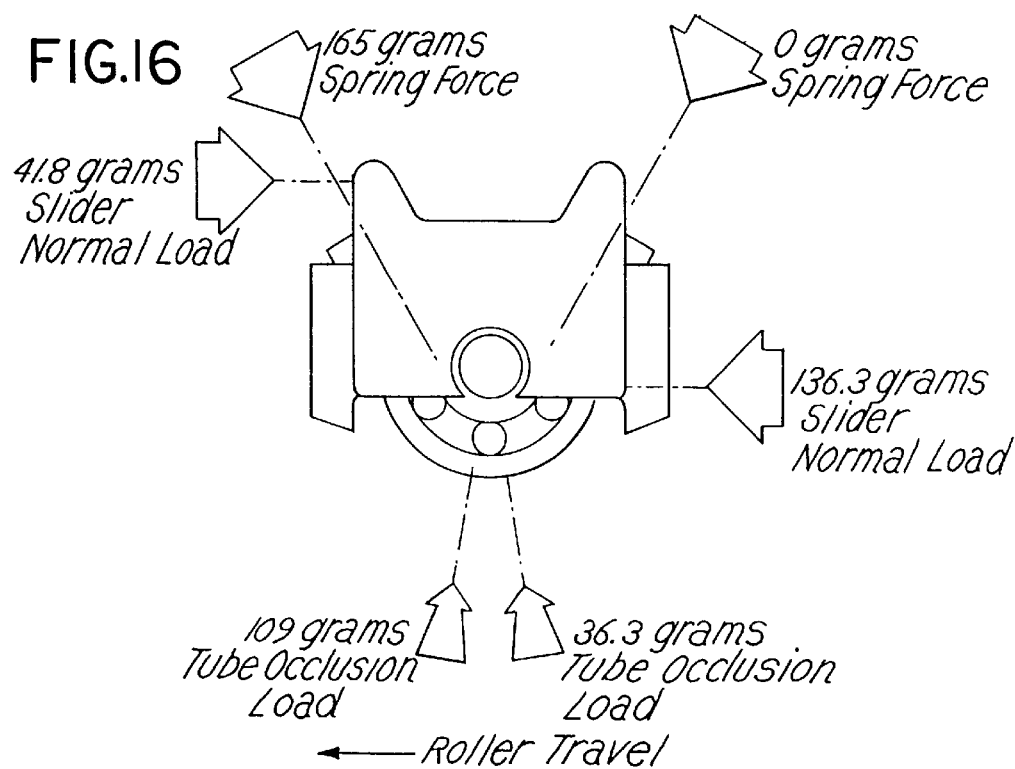

IMPLANTABLE DRUG DELIVERY DEVICE WITH PERISTALTIC PUMP HAVING A BOBBIN ROLLER ASSEMBLY

RELATED APPLICATIONS

The following applications are related to the present application: "Spring Loaded Implantable Drug Infusion Device", assigned Ser. No. 09/561,583 having Attorney Docket No. 11738.84231; and "Implantable Drug Delivery Device with Peristaltic Pump Having Retractable Rollers," assigned Ser. No. 09,834,874, having Attorney Docket No. 11738.86899.

FIELD OF THE INVENTION

The present invention relates to an implantable drug delivery device for infusing a therapeutic agent into an organism, and more particularly, relates to an improved peristaltic implantable pump with improved occlusion along a drug delivery pump tube.

BACKGROUND OF THE INVENTION

Implantable drug infusion devices are well known in the art. These devices typically include a medication reservoir within a generally cylindrical housing. Some form of fluid flow control is also provided to control or regulate the flow of fluid medication from the reservoir to the outlet of the device for delivery of the medication to the desired location in a body, usually through a catheter. These devices are used to provide patients with a prolonged dosage or infusion of a drug or other therapeutic agent.

Active drug infusion devices feature a pump or a metering system to deliver the drug into the patients system. An example of such a drug infusion pump currently available is the Medtronic SynchroMed programmable pump. Additionally, U.S. Pat. Nos. 4,692,147 (Duggan), 5,840,069 (Robinson), and 6,036,459 (Robinson), assigned to Medtronic, Inc., Minneapolis, Minn., disclose body-implantable electronic drug administration devices comprising a peristaltic (roller) pump for metering a measured amount of drug in response to an electronic pulse generated by control circuitry associated within the device. Each of these patents is incorporated herein by reference in their entirety for all purposes. Such devices typically include a drug reservoir, a fill port, a peristaltic pump having a motor and a pumphead to pump out the drug from the reservoir, and a catheter port to transport the drug from the reservoir via the pump to a patient's anatomy. The drug reservoir, fill port, peristaltic pump, and catheter port are generally held in a housing, or bulkhead. The bulkhead typically has a series of passages extending from the drug reservoir and through the peristaltic pump that lead to the catheter port, which is typically located on the side of the housing. The peristaltic pump comprises a pumphead having rollers, a race or cavity defined by the bulkhead, and a pump tube that is threaded or inserted between the rollers and the race. The peristaltic pumps use the rollers to move a drug through the pump tube from the drug reservoir to the catheter port. The drug is then pushed by the pump through a catheter connected to the catheter port, and is delivered to a targeted patient site from a distal end of the catheter.

The prior art delivery devices, however, are limiting in that the load that the rollers place on the tube can vary as the rollers move along the tube. If the load is excessive, excess energy will be consumed and the tube life will be shortened, resulting in increased replacement costs. If the load is insufficient, inadequate occlusion of the tube will result in leakage of fluid past the roller, reducing the accuracy of the pump. Variation in the load is caused by variations in the gap between the rollers and the race in which the pump tube lies, the gap variance being due to manufacturing tolerances associated with the tube, the race and the pumphead. Prior art solutions to the load variance problem include tight manufacturing tolerances, sorting and matching of components, and placing shims of appropriate thickness between the rollers and the tube, each of which increases manufacturing costs and reduces manufacturing flexibility.

It is an object of the present invention to provide an implantable drug infusion device which reduces or wholly overcomes some or all of the difficulties inherent in prior known devices. Particular objects and advantages of the invention will be apparent to those skilled in the art, that is, those who are knowledgeable or experienced in this field of technology, in view of the following disclosure of the invention and detailed description of preferred embodiments.

SUMMARY OF THE INVENTION

The present invention provides an implantable drug infusion device which features a peristaltic pump having a new configuration, in which a spring biases a roller assembly against a pump tube, thereby minimizing the variation in the load that the roller assembly places on the pump tube.

In accordance with a first aspect, an implantable drug infusion device comprises a peristaltic pump, including a pump tube for holding a liquid to be pumped. A race is configured to support the tube along a path. A roller assembly is configured to compress the tube against the race at one or more points along the path, and the roller assembly includes at least one roller. A drive assembly drives the roller assembly relative to the tube along the path so as to move the liquid through the tube. A biasing member is operably connected to the one roller to adjustably bias the roller against the tube.

In accordance with another aspect, an implantable drug infusion device includes a bulkhead having a race. A pump tube having an inlet and an outlet is positioned within the race, the race configured to support the tube along a path. A roller assembly is configured to compress the tube against the race at least one point along the path, and the roller assembly includes a hub and at least one roller biased against the pump tube. A drive assembly drives the roller assembly relative to the tube along the path so as to move a liquid through the tube. A biasing member is operably connected to the roller to adjustably bias the at least one roller against the tube.

In accordance with yet another aspect, an implantable drug infusion device includes a bulkhead having a race, a first chamber, and a second chamber. A pump tube has an inlet and an outlet and is positioned within the race, the race configured to support the tube along a path. A motor assembly is positioned within the first chamber, a pumphead assembly is positioned within the second chamber, and the motor assembly drives the pumphead assembly. A drive assembly drives the roller assembly relative to the tube along the path so the rollers compress the tube to move a liquid through the tube. A spring is operably connected to each roller assembly to bias a corresponding roller against the tube.

In accordance with another aspect, the pumphead assembly includes a roller assembly comprising at least two biasing members or springs operably connected to each roller to adjustably bias the roller against the pump tube, wherein the biasing members form an angle. This roller assembly provides biasing or spring loading to the rollers that provide occlusion to the pump tube and thus move a drug through the pump tube. In a preferred embodiment, the roller assembly comprises three rollers contained within three corresponding roller housings, each roller housing operably connected to the other two roller housings by a biasing member or spring. Thus, at each roller housing is a pair of operably connected biasing members or springs, which form an angle. This triangular arrangement of springs provides a compact design with a low spring rate at each roller. The low spring rate at each roller provides for low variations in occlusion load and for changes in roller distance from the pump shaft. This triangular spring arrangement can be characterized as a "live" bobbin roller assembly, wherein each roller housing is operably connected to an adjacent roller housing by a biasing member or spring. Further, components or parts for this bobbin roller assembly can be readily made using injection molding processing. More specifically, the parts that can be readily made using injection molding processing include an upper plate, a lower plate, and the three roller housings.

From the foregoing disclosure, it will be readily apparent to those skilled in the art, that is, those who are knowledgeable or experienced in this area of technology, that the present invention provides a significant advance over the prior art. Preferred embodiments of the implantable infusion device of the present invention can significantly reduce the variation in load placed by the roller assembly on the pump tube. This will allow for less stringent manufacturing tolerances, increased manufacturing flexibility, increased tube life, and improved performance. These and additional features and advantages of the invention disclosed here will be further understood from the following detailed disclosure of preferred embodiments.

BRIEF DESCRIPTION OF THE DRAWINGS

Preferred embodiments are described in detail below with reference to the appended drawings.

The accompanying drawings, which are incorporated into and form a part of this specification, together with the description, serve to explain the principles of the invention. The drawings are not drawn necessarily to scale, are only for the purpose of illustrating a preferred embodiment of the invention, and are not to be construed as limiting the invention. Some features of the implantable drug delivery device depicted in the drawings have been enlarged or distorted relative to others to facilitate explanation and understanding. The above mentioned and other advantages and features of the invention will become apparent upon reading the following detailed description and referring to the accompanying drawings in which like numbers refer to like parts throughout and in which:

FIG. 15 illustrates bobbin housing loads with leading spring 10% low in load and lagging spring 10% high in load; and FIG. 16 illustrates bobbin housing loads for the condition of lagging spring removed.

DESCRIPTION OF THE PREFERRED EMBODIMENTS

Figure 1:
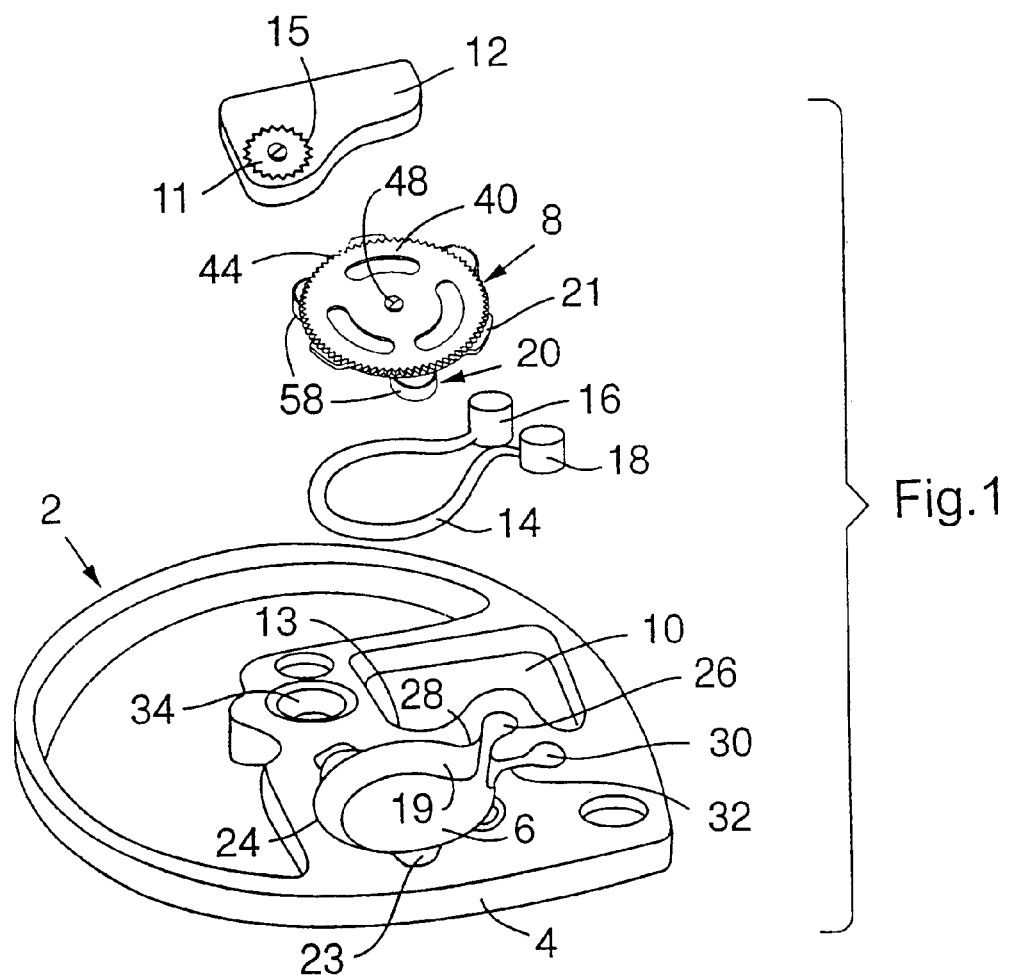
FIG. 1 is an exploded perspective view of an implantable drug delivery device in accordance with the present invention.

As shown in FIG. 1, an implantable drug delivery device 2 in accordance with the invention comprises a bulkhead 4 containing a number of chambers and cavities sized and configured to house various subsystems of the implantable drug infusion device. In particular, bulkhead 4 has a first chamber 6 sized and configured to house a peristaltic pumphead assembly 8. A second chamber 10, sized and configured to house a motor assembly 12 which drives pumphead assembly 8, is positioned adjacent first chamber 6 and separated therefrom by a wall 13. Other chambers of bulkhead 4 house a battery and the electronic circuitry (not shown) used to operate implantable drug infusion device 2 and to control the dosage rate of the medication into the body.

Pumphead assembly 8 includes a compression member, such as roller arm assembly 20, for compressing a pump tube 14 having an inlet 16 and an outlet 18. First chamber 6 has a generally circular wall 24 defining a pump race 19. Pump tube 14 is placed in first chamber 6 in close proximity to wall 24 so that roller arm assembly 20 may force the tube against the wall, thereby forcing medication to move through the tube in a known peristaltic manner. Flanges 21 extending outwardly from pumphead assembly 8 are received in recesses 23 formed in first chamber 6, supporting pumphead assembly 8 in first chamber 6. Inlet 16 is placed in a pump inlet cavity 26 formed in bulkhead 4. Pump inlet cavity 26 is connected to the pump race 19 by a pump inlet race ramp 28. Pump tube outlet 18 is placed in a pump outlet cavity 30 formed in bulkhead 4. Pump tube outlet cavity 30 is connected to the pump race 19 by a pump outlet race ramp 32. In a preferred embodiment, both pump inlet race ramp 28 and pump outlet race ramp 32 have an arcuate geometry to reduce pumphead torque as described in greater detail below. A cover (not shown) is also provided for bulkhead 4 to provide protection for the components of drug infusion device 2. Motor assembly 12 includes a motor (not shown)

which drives a four-stage gear assembly 11, only the fourth stage of which is visible. Teeth 15 are formed on the periphery of the fourth stage of gear assembly 11.

Bulkhead 4 has an integral fill port cavity 34, sized and configured to house a septum and components to retain the septum. Drugs are injected through the septum to fill a reservoir (not shown) contained within a lower portion of bulkhead 4. A pathway is formed between the reservoir and pump inlet cavity 26, through which drugs are introduced into pump tube 14. The drugs exit pump outlet cavity 30 and travel through another pathway formed in bulkhead 4 to a catheter port on the periphery of bulkhead 4 from which the drug exits the device 2 and enters the anatomy of the individual. The structure of the septum, retaining components, pathways, and catheter port are known to one of skill in the art and are not shown here.

Figure 2:
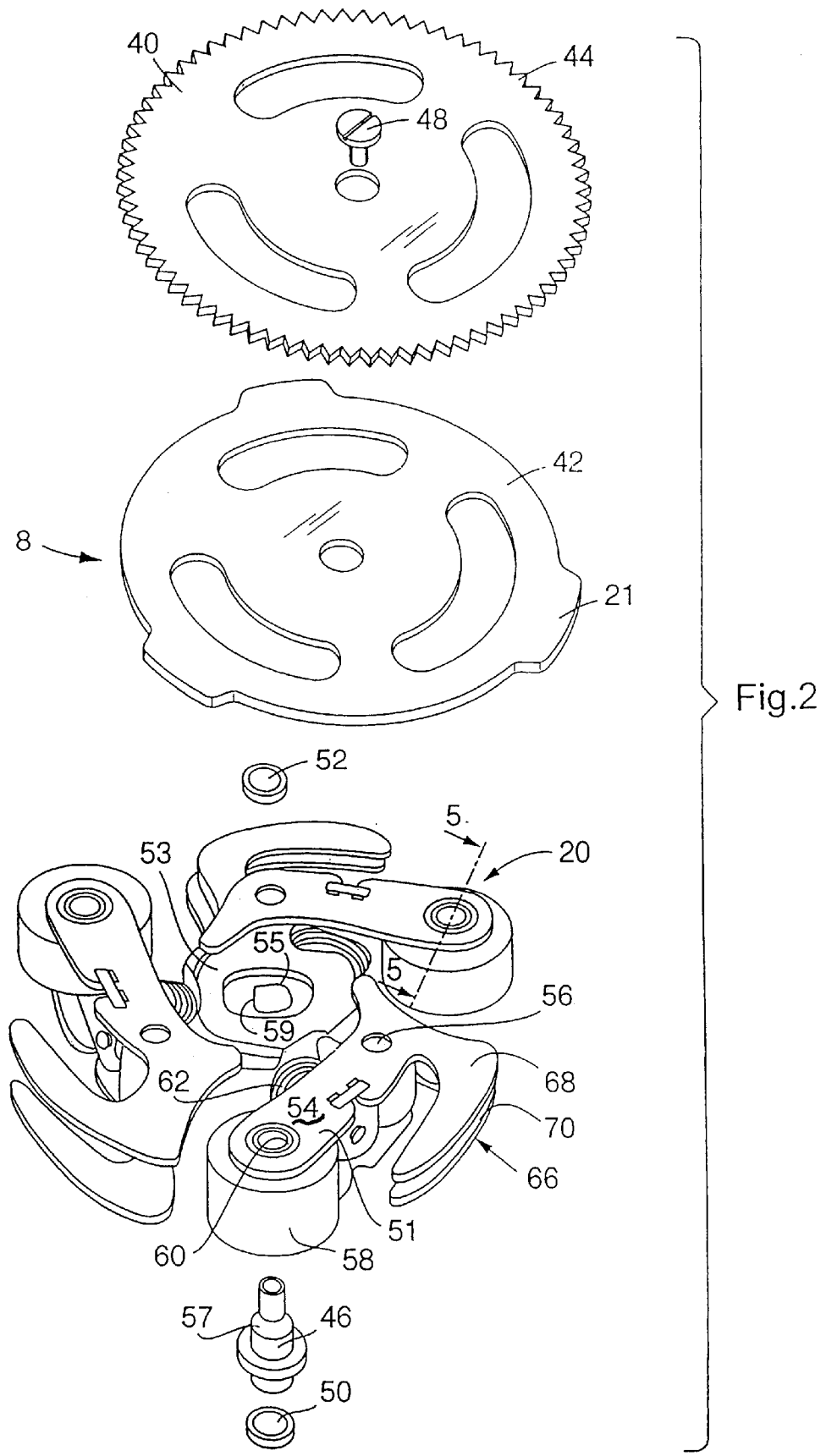
FIG. 2 is an exploded perspective view of a pumphead assembly of the implantable device of FIG. 1.

Referring now to FIG. 2, pumphead assembly 8 is shown in exploded form. Pumphead assembly 8 includes a drive gear 40 with teeth 44 formed about its periphery. A support plate 42 is positioned below drive gear 40. Flanges 21 extend outwardly from support plate 42 and, as described above, are received in recesses 23 of bulkhead 4, and preferably welded thereto. Roller arm assembly 20 is positioned below support plate 42. Drive shaft 46 extends axially through apertures in roller arm assembly 20, support plate 42, and drive gear 40, and is retained by retaining screw 48. Drive shaft 46 is supported for rotation at its lower end by lower bearing 50, and at a central location, between roller arm assembly 20 and support plate 42, by upper bearing 52.

Figure 5:
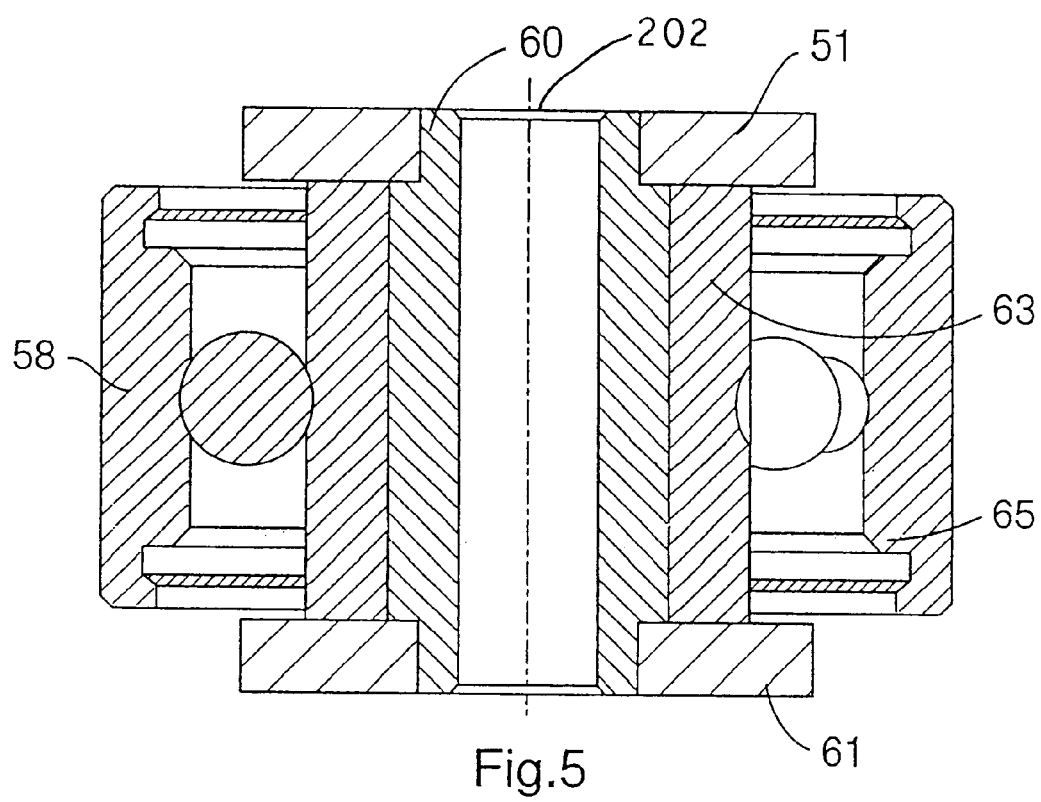
FIG. 5 is a section view, taken along lines 5—5 of FIG. 2, of a retracting roller arm of the implantable device of FIG. 1.

Roller arm assembly 20 comprises a central hub 53 having an aperture 55 through which drive shaft 46 extends. Flat 57 on drive shaft 46 mates with flat 59 of aperture 55 such that roller arm assembly 20 rotates as drive shaft 46 rotates. A plurality of roller arms 54 are each pivotally secured by a pin 56 to hub 53. Each roller arm 54 comprises upper plate 51 and lower plate 61. A roller 58 is pivotally secured to each roller arm 54 by an axle 60. As seen in FIG. 5, axle 60 extends between upper plate 51 and corresponding lower plate 61. Axle 60 passes through an inner race (not shown) of roller 58. In the illustrated embodiment, roller arm assembly 20 is shown with three roller arms 54 and three corresponding rollers 58, however, the number of roller arms 54 and rollers 58 may be greater or lesser than three.

Figure 3:
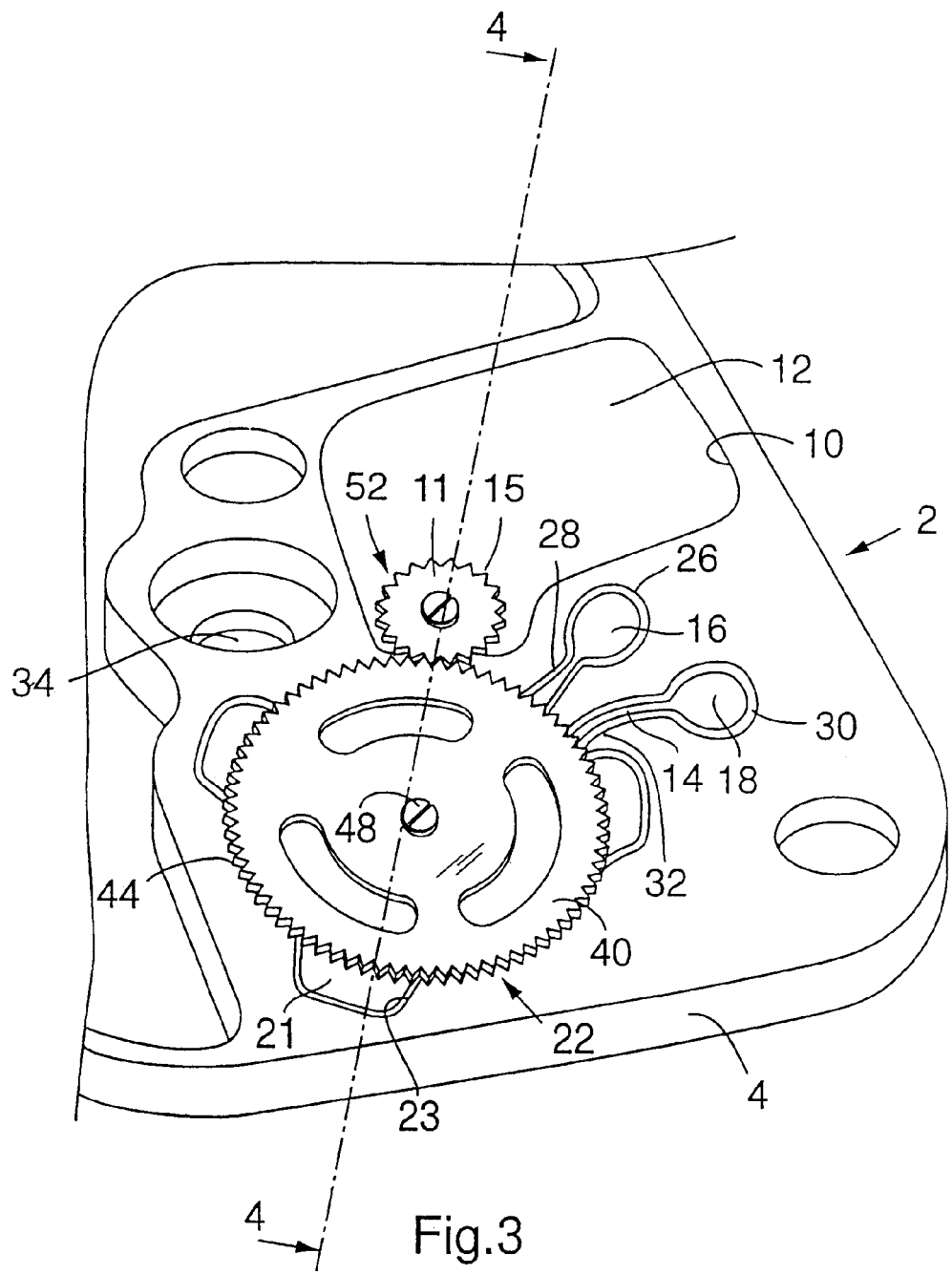
FIG. 3 is perspective view, partially cut away, of the implantable device of FIG. 1 shown in its assembled state.
Figure 4:
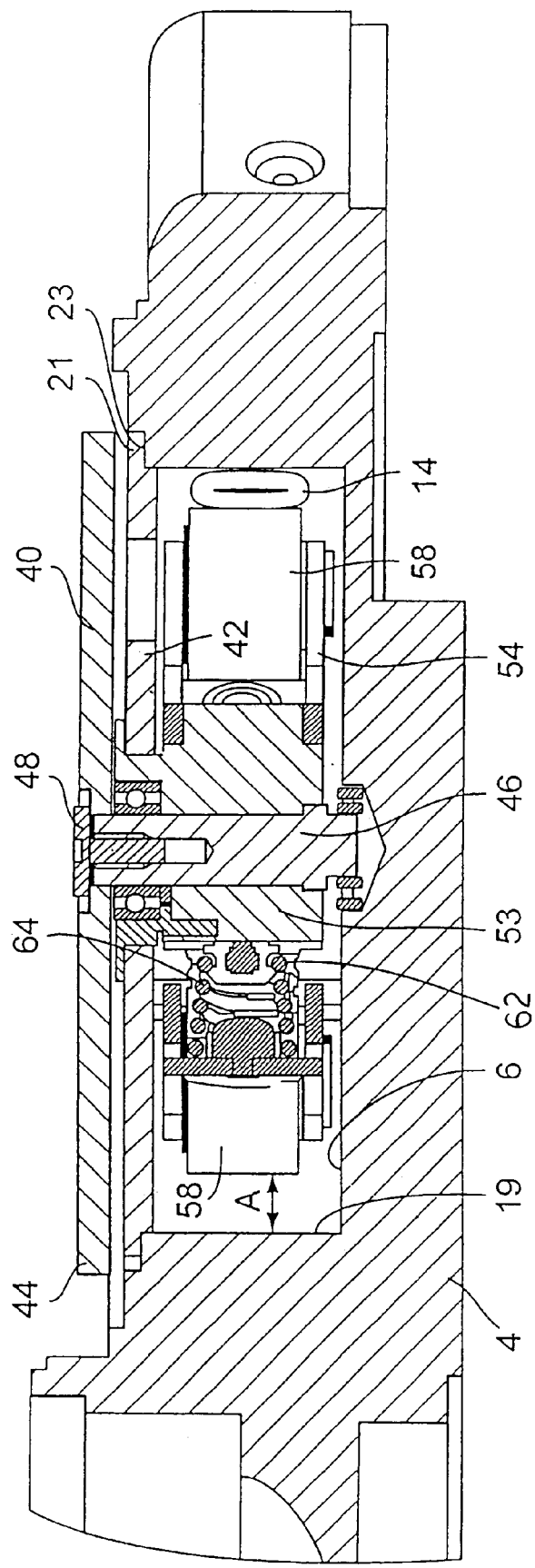
FIG. 4 is a section view, taken along lines 4—4 of FIG. 3, of the implantable device of FIG. 1.

As seen in FIGS. 3 and 4, teeth 15 of gear assembly 11 drivingly engage teeth 44 of drive gear 40, thereby causing rollers 58 to move about race 19, compressing and occluding tube 14 as they move and forcing the drug therethrough in known peristaltic fashion. As noted above, inlet race ramp 28 and outlet race ramp 32 each have an arcuate geometry, which reduces the torque required as each roller 58 engages pump tube 14 during rotation of roller arm assembly 20.

Referring back to FIG. 2, each roller arm 54 and its corresponding roller 58 is adjustably biased outwardly by a biasing member, such as spring 62. In a preferred embodiment, spring 62 is a coil spring. As seen in FIG. 4, spring 62 is oriented to facilitate the occlusion, or compression, of tube 14 by roller 58. Since manufacturing tolerances on the system components, i.e., roller 58, tube 14 and race 19, can result in variations in the gap A between roller 58 and race 19, the biasing action of spring 62 can advantageously minimize the variation in load placed by roller 58 on tube 14, greatly increasing the compliance of the system. Thus, for an incremental change in the gap between roller 58 and race 19, the incremental load required is reduced. For example, in prior art devices, where the system compliance is accounted for by the tube itself, a 0.001" decrease in a radial direction of the race could incur a 150 g load increase on roller 58. With the present invention, however, spring 62 may be sized with a spring rate such that for a 0.001" decrease in the race, a 1.5 g increase in load is realized. In a preferred embodiment, spring 62 is formed of a highly corrosion resistant and fatigue resistant alloy. Suitable materials for biasing member or spring 62 include cobalt and stainless steel alloys. In other preferred embodiments, a nitinol shape memory alloy may be used for spring 62.

The biasing member provides numerous advantages over the prior art devices. Reducing the variation in load prevents excessive loading, thereby providing increased tube life; minimizes the force needed to occlude the pump tube, thereby minimizing the torque requirement for occlusion; improves occlusion and, therefore, reducing leakage and improving the performance of the peristaltic pump; allows for looser manufacturing tolerances and minimizes the need for sorting and matching components, providing increased manufacturing flexibility and reducing costs.

In an embodiment, as seen in FIG. 2, roller arm assembly 20 further includes a tube guide 66. In the illustrated embodiment, tube guide 66 is connected to roller arm 54 and is formed of an upper plate 68 and a lower plate 70. In another embodiment, tube guide 66 may be connected directly to hub 53. Tube guide 66 serves to help keep pump tube 14 properly aligned to ensure that rollers 58 are centered with respect to pump tube 14.

Figure 6:
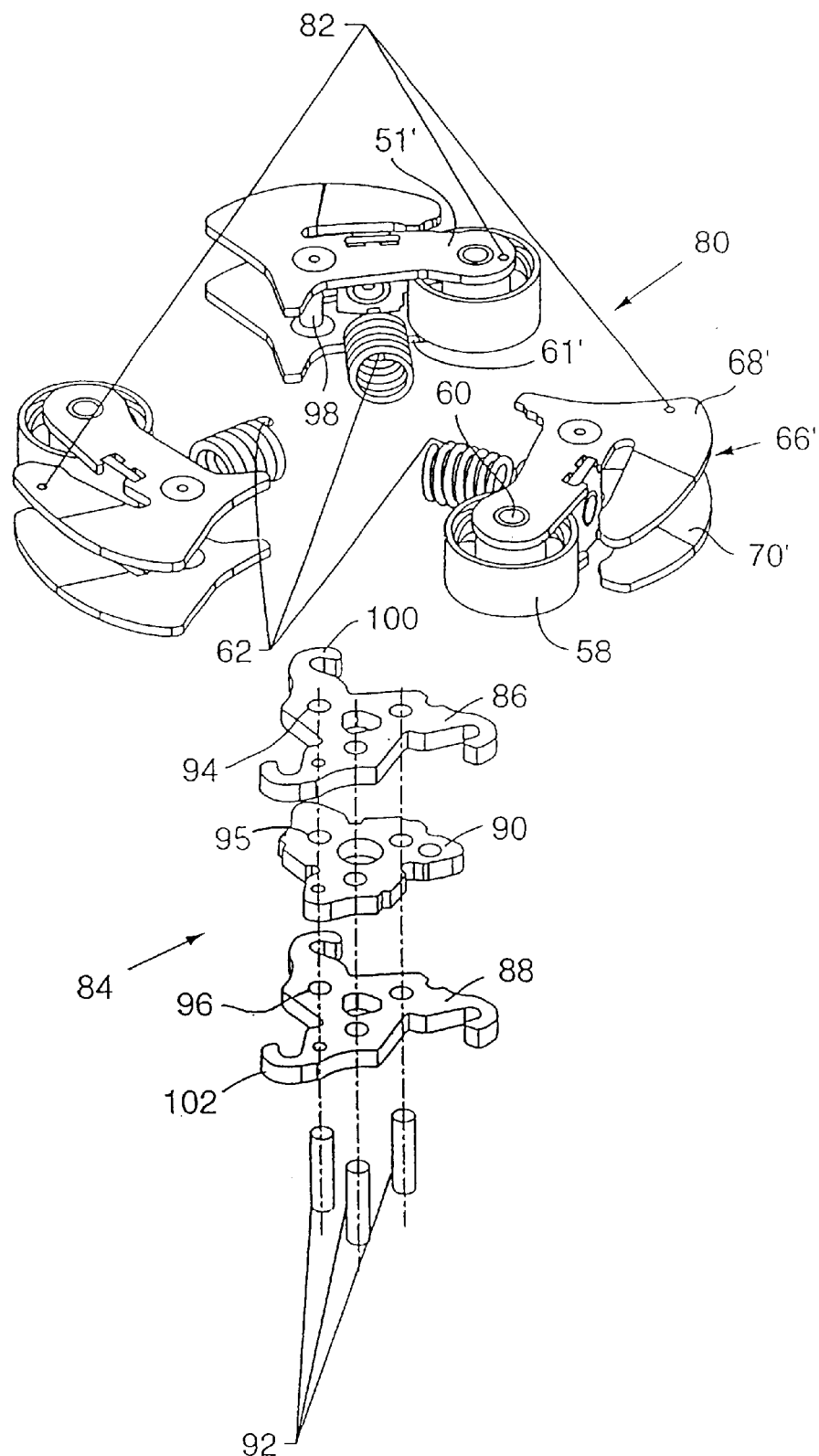
FIG. 6 is an exploded perspective view of an alternative embodiment of the roller arm assembly of FIG. 1.

Another embodiment of a roller arm assembly 80 is shown in FIG. 6. Roller arm assembly 80 comprises three roller arms 82 pivotally secured to a hub 84. Hub 84 comprises upper plate 86, lower plate 88, and center plate 90. Rods 92 extend through apertures 94, 95, and 96 formed in upper plate 86, center plate 90, and lower plate 88, respectively. Pivot pins 98 extend between upper plate 51' and lower plate 61' of each roller arm 82. Hooks 100, 102 formed on upper plate 86 and lower plate 88, respectively, of hub 84, capture pivot pins 98. The force of springs 62 acting on roller arms 82 helps maintain roller arms 82 in position on hub 84.

Figure 7:
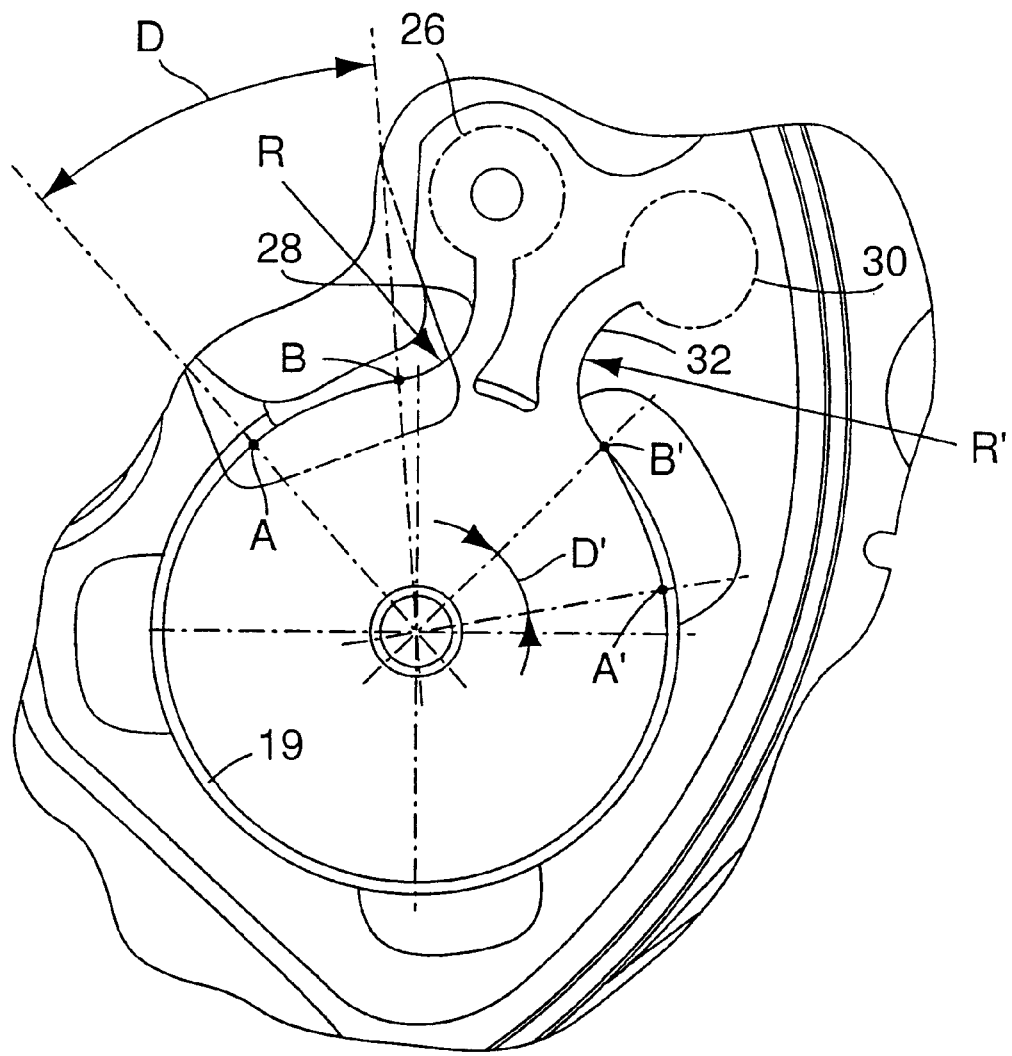
FIG. 7 is a plan view of the geometry of the race and inlet and outlet ramps of the implantable device of FIG. 1.

In a preferred embodiment, inlet and outlet ramps 28 and 32 have exit and entry ramps transitioning smoothly into and from race 19 in order to minimize drag torque on pumphead assembly 8. As seen in FIG. 7, inlet ramp 28 transitions smoothly from a radius R of approximately 3.947 mm (0.1554 in) through point B to point A of race 19. Race 19 then transitions from point A' to point B and then through a radius R☐ of approximately 4.02 mm (0.1583 mm). The angles D, D' between points A and B, and A☐ and B☐, respectively are approximately 35.5 degrees. Shown in the table below are the dimensions for the radius of race 19 along the arc between points A and B, and A☐ and B☐, in 0.5 degree increments. It is to be appreciated that the radius varies smoothly along race 19.

| Angle (degrees) | Radius  |
|-----------------|---------|
| 0.0°            | 11.0000 |
| .5              | 11.0054 |
| 1.0             | 11.0108 |
| 1.5             | 11.0162 |
| 2.0             | 11.0216 |
| 2.5             | 11.0270 |
| 3.0             | 11.0324 |

-continued

| Angle (degrees) | Radius |
| --- | --- |
| 3.5 | 11.0378 |
| 4.0 | 11.0432 |
| 4.5 | 11.0486 |
| 5.0 | 11.0540 |
| 5.5 | 11.0594 |
| 6.0 | 11.0648 |
| 6.5 | 11.0702 |
| 7.0 | 11.0756 |
| 7.5 | 11.0810 |
| 8.0 | 11.0864 |
| 8.5 | 11.0918 |
| 9.0 | 11.0972 |
| 9.5 | 11.1026 |
| 10.0 | 11.1080 |
| 10.5 | 11.1134 |
| 11.0 | 11.1188 |
| 11.5 | 11.1242 |
| 12.0 | 11.1296 |
| 12.5 | 11.1350 |
| 13.0 | 11.1404 |
| 13.5 | 11.1458 |
| 14.0 | 11.1512 |
| 14.5 | 11.1566 |
| 15.0 | 11.1620 |
| 15.5 | 11.1674 |
| 16.0 | 11.1728 |
| 16.5 | 11.1782 |
| 17.0 | 11.1836 |
| 17.5 | 11.1890 |
| 18.0 | 11.1944 |
| 18.5 | 11.1998 |
| 19.0 | 11.2052 |
| 19.5 | 11.2106 |
| 20.0 | 11.2160 |
| 20.5 | 11.2214 |
| 21.0 | 11.2268 |
| 21.5 | 11.2322 |
| 22.0 | 11.2376 |
| 22.5 | 11.2430 |
| 23.0 | 11.2484 |
| 23.5 | 11.2538 |
| 24.0 | 11.2592 |
| 24.5 | 11.2646 |
| 25.0 | 11.2700 |
| 25.5 | 11.2754 |
| 26.0 | 11.2808 |
| 26.5 | 11.2862 |
| 27.0 | 11.2916 |
| 27.5 | 11.2970 |
| 28.0 | 11.3024 |
| 28.5 | 11.3078 |
| 29.0 | 11.3132 |
| 29.5 | 11.3186 |
| 30.0 | 11.3240 |
| 30.5 | 11.3294 |
| 31.0 | 11.3348 |
| 31.5 | 11.3402 |
| 32.0 | 11.3456 |
| 32.5 | 11.3510 |
| 33.0 | 11.3564 |
| 33.5 | 11.3618 |
| 34.0 | 11.3672 |
| 34.5 | 11.3726 |
| 35.0 | 11.3780 |
| 35.5 | 11.3834 |

An alternative embodiment, which can be referred to as the bobbin embodiment, is illustrated in FIGS. 8 through 16. In this embodiment, a roller assembly 500 is assembled and can replace roller arm assembly 20 in FIG. 2. Thus, roller assembly 500 is configured to compress pump tube 14 against the race 19 at one or more points along a path. The roller assembly 500 comprises at least one roller 404, and at least two biasing members or springs 402 operably connected to the roller 404 to adjustably bias the roller 404 against the tube 14. The two biasing members 402 form an angle 501. Further, roller housings 400 are connected to at least one adjacent roller housing 400 by a spring 402.

As illustrated in FIGS. 8 through 12, rollers 404 are positioned within a corresponding roller housing 400. In this embodiment, rollers 404, roller pins 405, roller housings 400 and springs 402 are positioned between a lower plate 406 and an upper plate 408. Lower plate 406 and upper plate 408 define openings 409 to receive portions 410 and 412 of roller housings 400, respectively. Portions 410 and 412 of roller housings 400 are positioned within openings 409 and are nearly flush with bottom surface 414 of bottom plate 406, and top surface 416 of upper plate 408, respectively. Roller pins 405 can be pressed or staked into roller housing 400, with spacers 407 providing a gap between roller 404 and roller housing 400.

Figure 8:
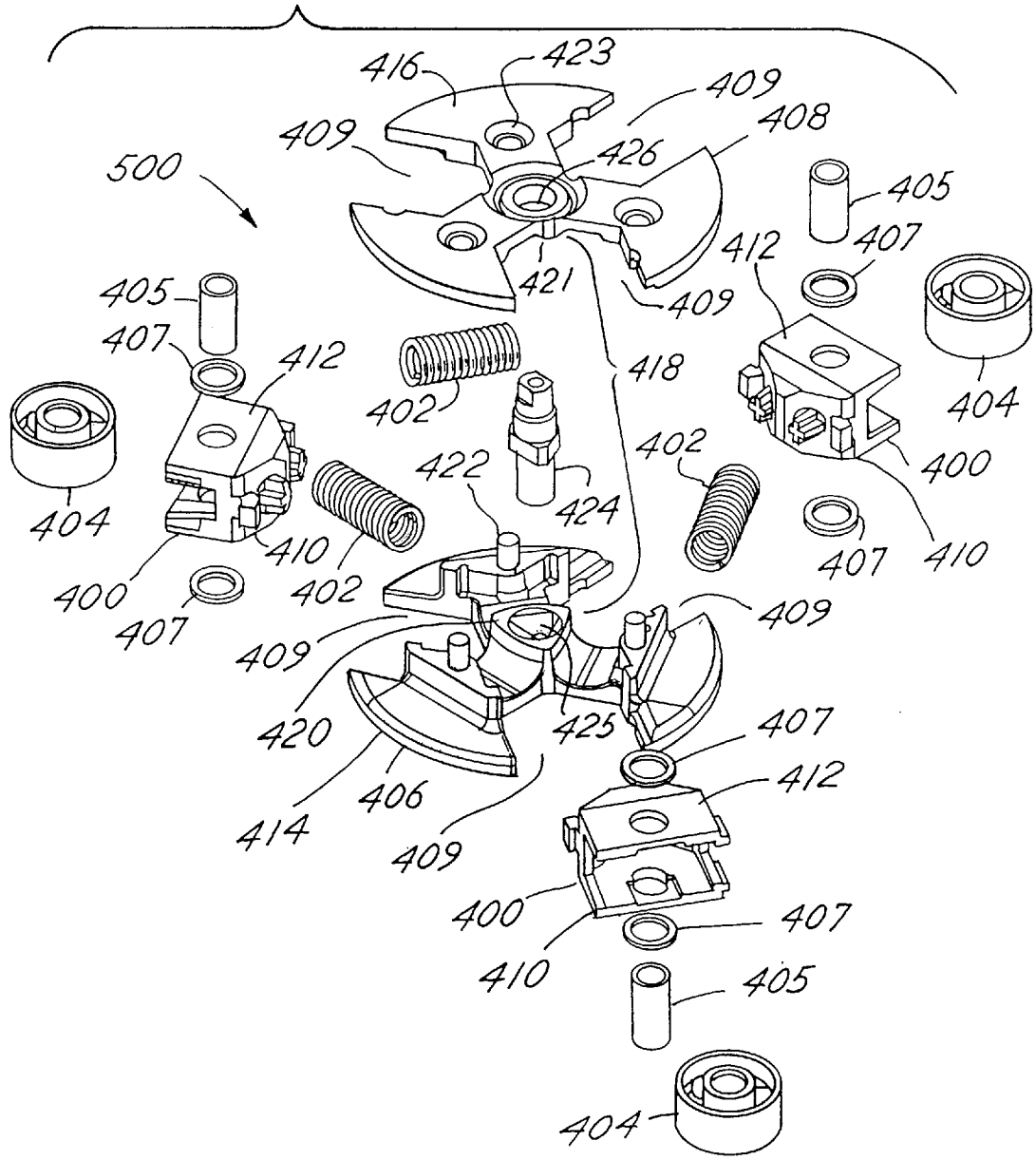
FIG. 8 is an exploded perspective view of an alternative embodiment, sometimes referred to herein as the bobbin embodiment, to the roller arm assembly 20 shown in FIG. 2.
Figure 9:
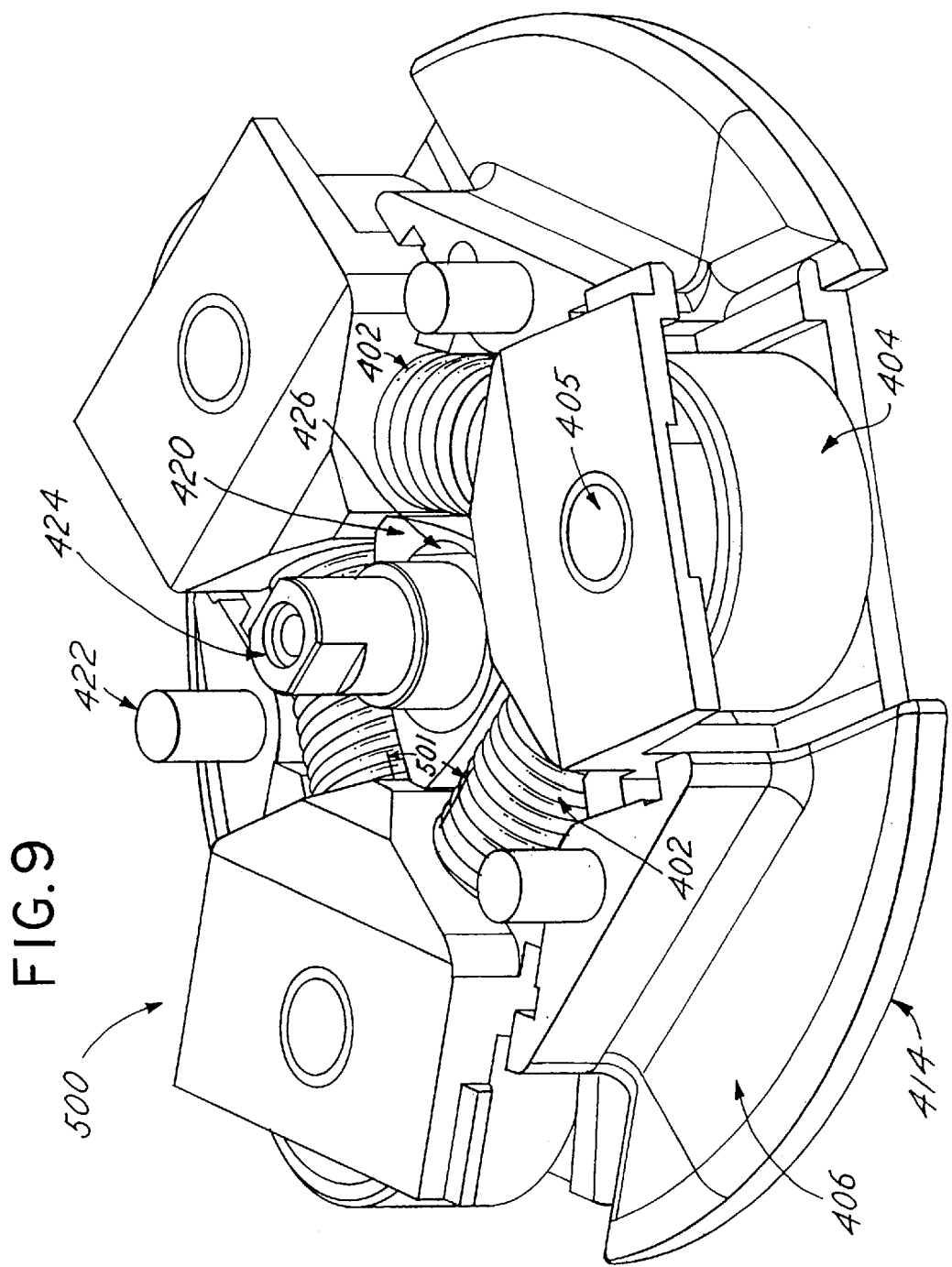
FIG. 9 is a perspective view of the bobbin embodiment shown in FIG. 8 as assembled, without an upper plate shown.
Figure 10:
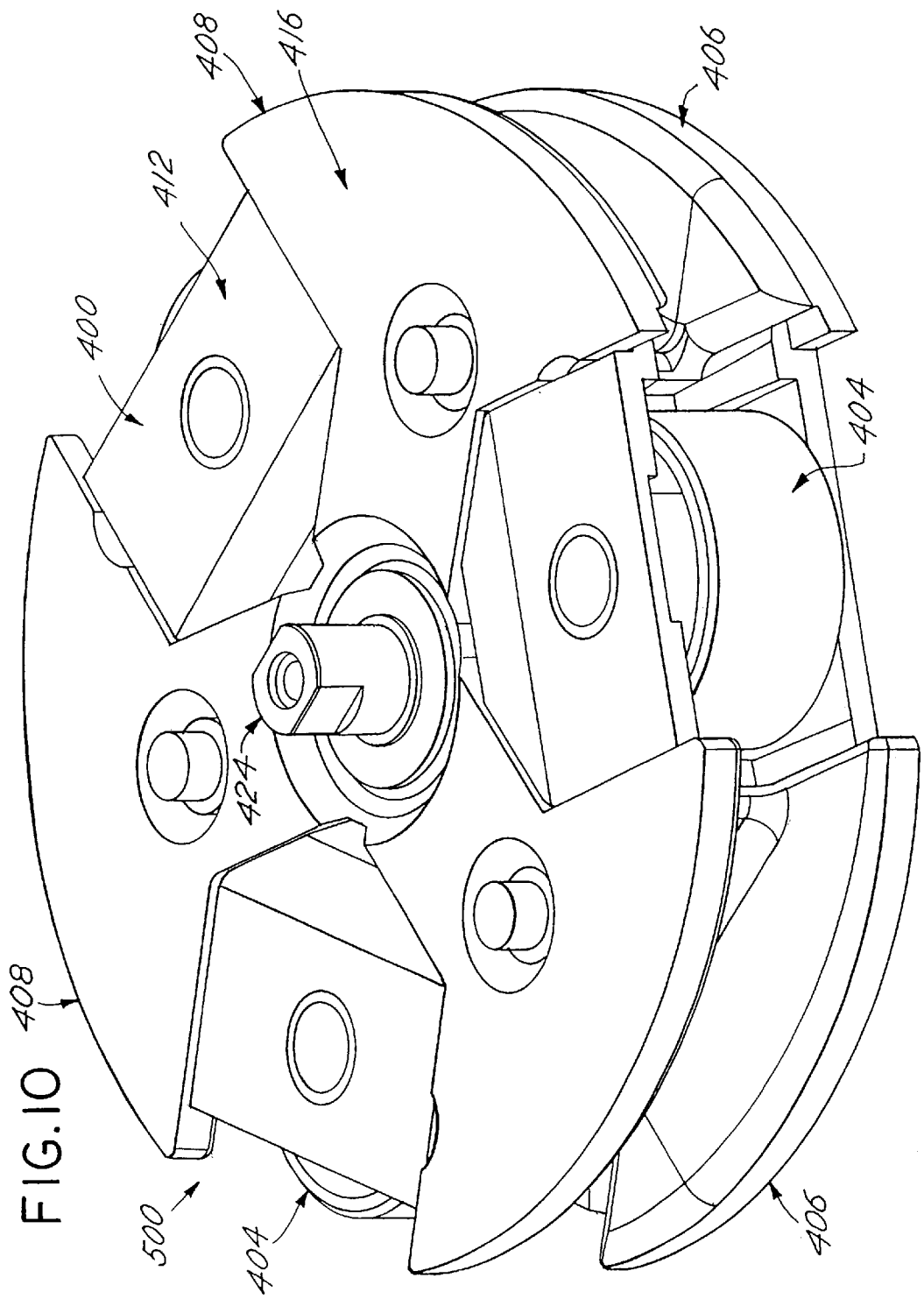
FIG. 10 is a perspective view of the bobbin embodiment of the present invention shown in FIG. 9, illustrating the attachment of an upper plate.
Figure 11:
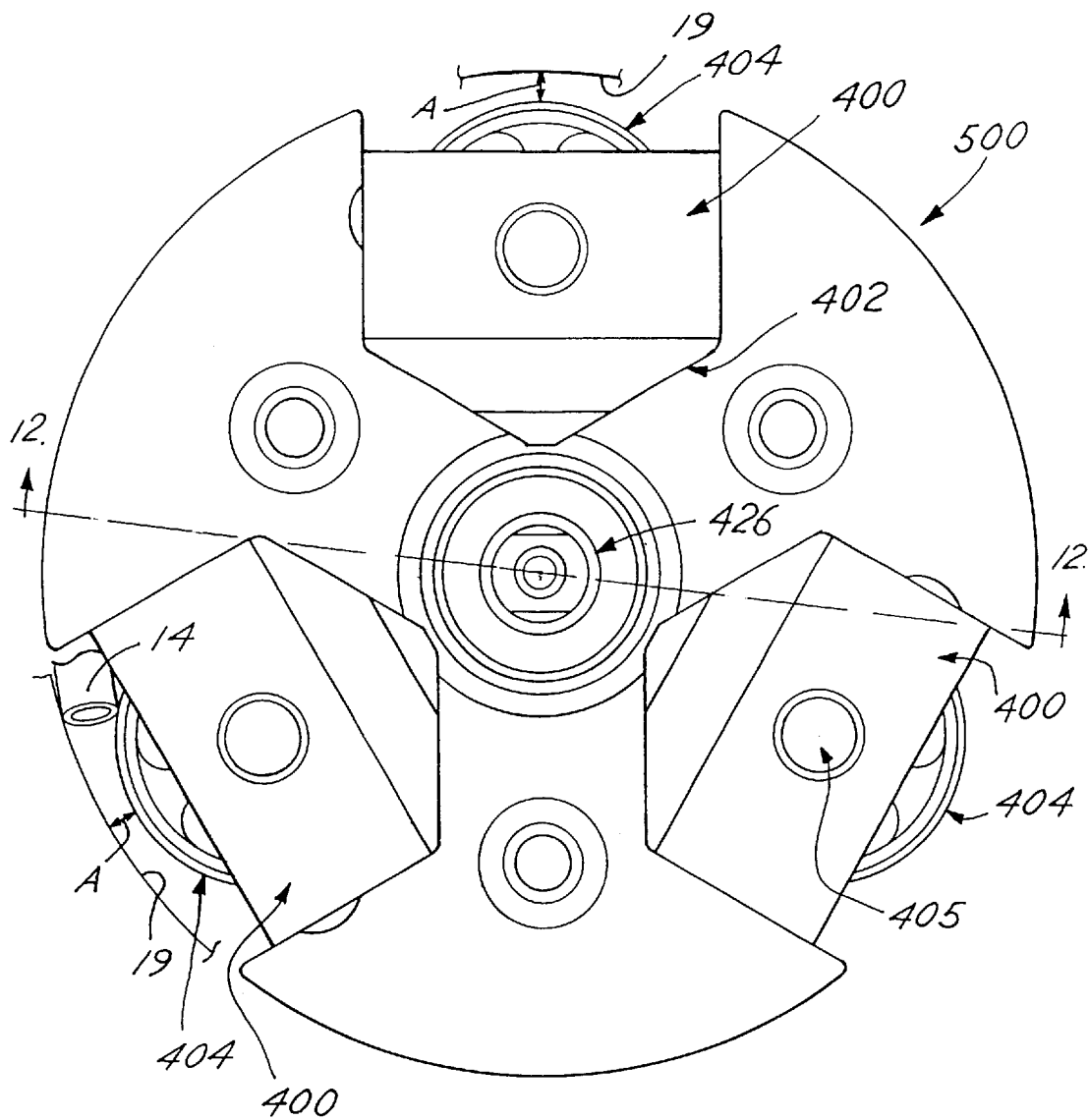
FIG. 11 is a top view of the bobbin embodiment illustrated in FIG. 10.
Figure 12:
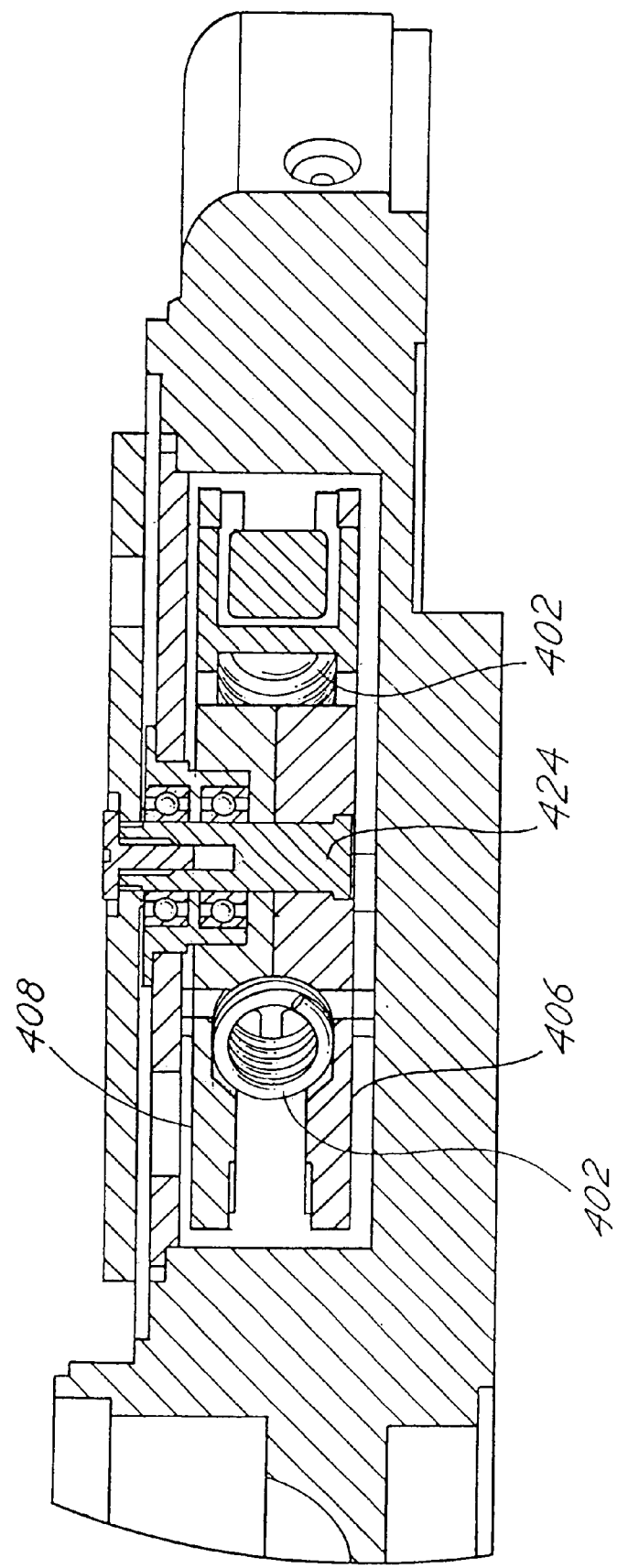
FIG. 12 is section view, taken along lines 12—12 of FIG. 11.

Hub 418 is comprised of portion 420 of bottom plate 406 and portion 421 of upper plate 408. Portions 420 and 421 can mate with each other via mating member 422 of bottom plate 406 and a corresponding mating member 423 of upper plate 408. FIG. 8 shows each mating member 423 lined up and between the center of hub 418 and a corresponding roller pin 405 to form a straight line. This embodiment provides structure to encapsulate springs 402 to avoid potential contact between springs 402 and pump tube 14. Shaft 424 can be placed through hole 425 defined in bottom plate 406 and through hole 426 in top plate 408. Shaft 424 can be driven by a drive assembly (not shown) as described in the preceding embodiments.

Figure 13:
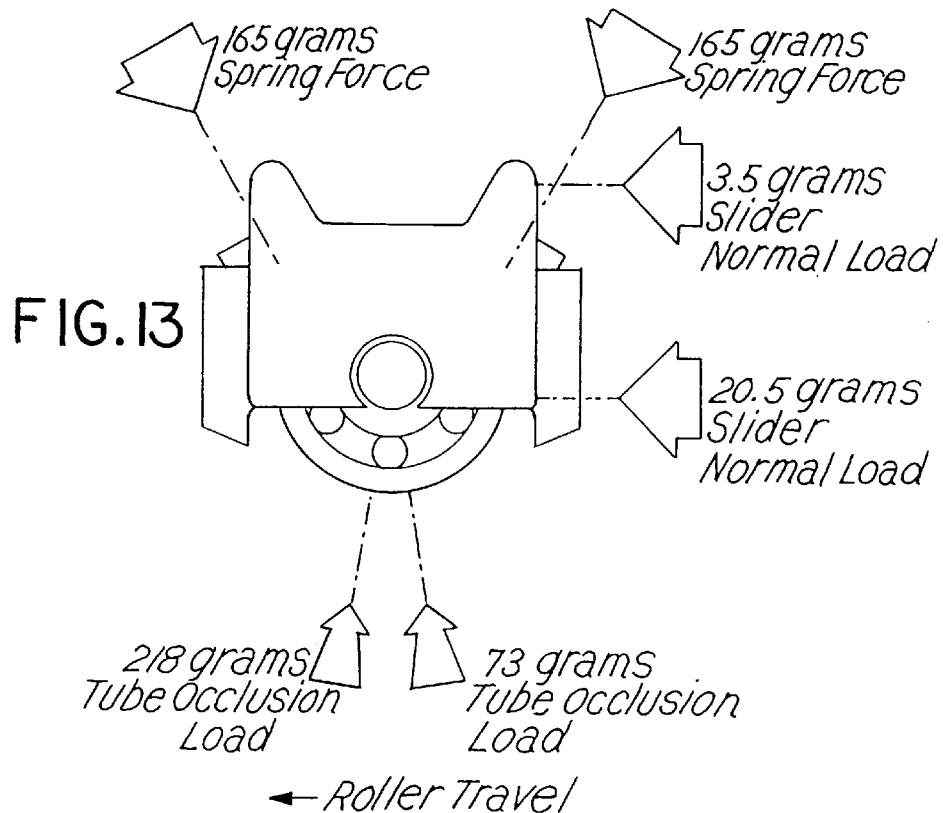
FIG. 13 illustrates roller bobbin housing loads for the condition of nominal spring loads.

FIG. 13 illustrates roller bobbin housing loads for the condition of nominal spring loads.

Figure 14:
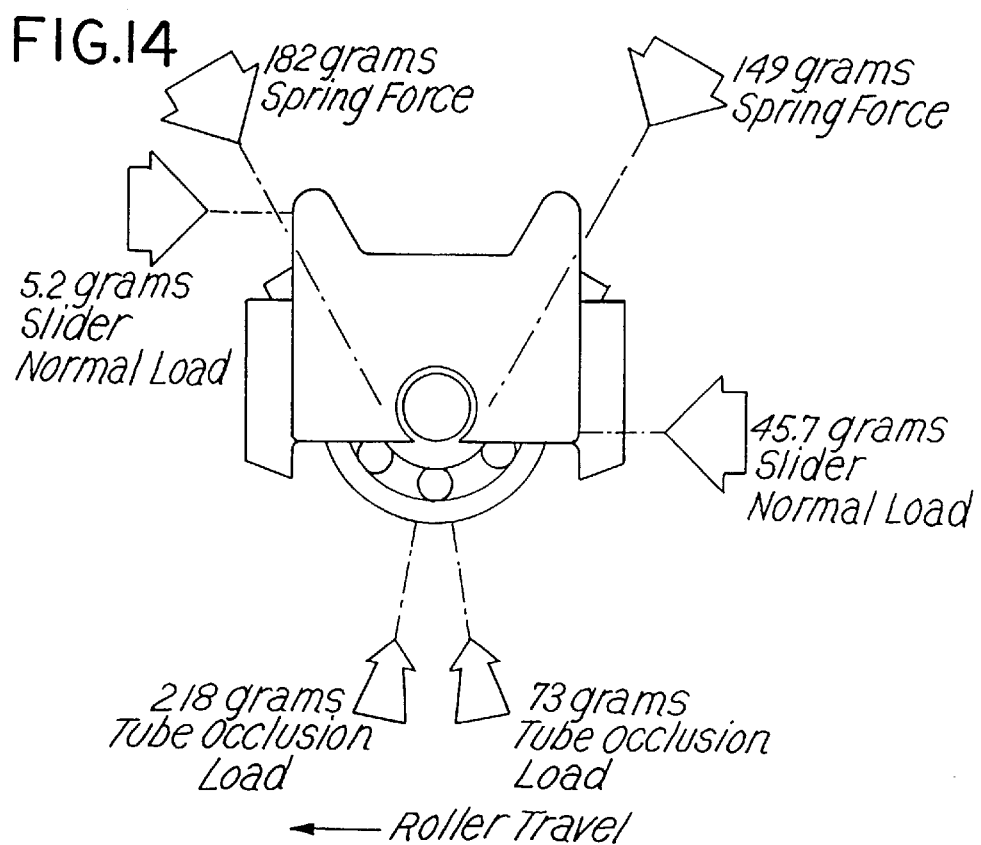
FIG. 14 illustrates bobbin housing loads with lagging spring 10% low in load and leading spring 10% high in load.

FIG. 14, illustrates bobbin housing loads with lagging spring 10% low in load and leading spring 10% high in load.

FIG. 15 illustrates bobbin housing loads with leading spring 10% low in load and lagging spring 10% high in load.

FIG. 16 illustrates bobbin housing loads for the condition of lagging spring removed.

Referring back to FIGS. 8 through 12, each roller housing 400 and its corresponding roller 404 is adjustably biased outwardly by at least two biasing members or springs 402. In addition, roller housings 400 can also be operably connected to hub 418, such as by springs similar to springs 402, including springs 62 as shown in FIGS. 2, 4, and 6.

In a preferred embodiment, spring 402 is a coil spring. In a preferred embodiment, spring 402 is formed of a material selected from the group consisting of cobalt, stainless steel or a nitinol shape memory alloy.

As shown in FIGS. 8–12, at least two springs 402 are oriented to facilitate the occlusion, or compression, of pump tube 14 by a roller 404. Since manufacturing tolerances on the system components, i.e., roller 404, tube 14 and race 19, can result in variations in the gap A between roller 404 and race 19, the biasing action of spring 402 can advantageously minimize the variation in load placed by roller 404 on tube 14, greatly increasing the compliance of the system. Thus, for an incremental change in the gap between roller 404 and race 19, the incremental load required is reduced. For example, in prior art devices, where the system compliance is accounted for by the tube itself, a 0.001" decrease in a radial direction of the race could incur a 150 g load increase on roller 404. With the present invention, however, spring 402 may be sized with a spring rate such that for a 0.001" decrease in the race, a 1.5 g or less increase in load is realized.

The bobbin embodiments illustrated in FIGS. 8 through 16, and as described above, provides numerous advantages over the prior art devices. Reducing the variation in load (a) prevents excessive loading, thereby providing increased tube life, and minimizes the force needed to occlude the pump tube, thereby minimizing the torque requirement for occlusion; (b) improves occlusion therefore, reducing leakage and improving the performance of the peristaltic pump; and (c) allows for looser manufacturing tolerances and minimizes the need for sorting and matching components, providing increased manufacturing flexibility and reducing costs.

It is to be appreciated that other roller arm and/or bobbin assembly constructions will be suitable, and are considered within the scope of the present invention. Suitable roller arm and/or bobbin assembly constructions will provide a biasing member or combination of biasing members to ensure that a roller, or other suitable compression member, is biased against a pump tube, thereby minimizing the variation in load required to occlude the pump tube.

Other suitable biasing members include, for example, leaf springs and springs of other constructions, elastomeric members, closed or open cell elastomeric foam members, torsion bars, magnetic members, and solenoids.

In light of the foregoing disclosure of the invention and description of the preferred embodiments, those skilled in this area of technology will readily understand that various modifications and adaptations can be made without departing from the scope and spirit of the invention. All such modifications and adaptations are intended to be covered by the following claims.

What is claimed is:

1. An implantable drug infusion device comprising, in combination:
    a pump tube for holding a liquid to be pumped;
    a race configured to support the tube along a path;
    a roller assembly configured to compress the tube against the race at one or more points along the path, the roller assembly including at least one roller, the roller assembly comprising at least two biasing members operably connected to the roller to adjustably bias the roller against the tube, the two biasing members forming an angle; and
    a drive assembly to drive the roller assembly relative to the tube along the path so as to move the liquid through the tube.

2. The implantable drug infusion device of claim 1, wherein at least one of the biasing members comprises a coil spring.

3. The implantable drug infusion device of claim 1, wherein at least one of the biasing members is made from a material selected from the group consisting of cobalt, stainless steel, and nitinol shape memory alloy.

4. The implantable drug infusion device of claim 1, wherein the two biasing members each comprises a coil spring.

5. The implantable drug infusion device of claim 4, wherein the two biasing members are made from a material selected from the group consisting of cobalt, stainless steel, and nitinol shape memory alloy.

6. The implantable drug infusion device of claim 1, wherein the race includes an inlet ramp and an outlet ramp.

7. The implantable drug infusion device of claim 6, wherein the inlet ramp has an arcuate geometry.

8. The implantable drug infusion device of claim 6, wherein the outlet ramp has an arcuate geometry.

9. The implantable drug infusion device of claim 1, wherein the roller assembly comprises at least one roller housing operably connected to the two biasing members, each roller housing having a roller secured thereto.

10. The implantable drug infusion device of claim 9, wherein the roller assembly comprises three roller housings and three rollers.

11. The implantable drug infusion device of claim 10, wherein each biasing member comprises a coil spring.

12. The implantable drug infusion device of claim 9, wherein at least one of the biasing members is made from a material selected from the group consisting of cobalt, stainless steel, and nitinol shape memory alloy.

13. The implantable drug infusion device of claim 1, wherein the drive assembly comprises a drive shaft and a drive gear, the drive gear configured to be rotatably driven by a motor, the drive shaft rotatably driven by the drive gear and rotatably driving the roller assembly.

14. The implantable drug infusion device of claim 13, wherein the drive gear includes a plurality of teeth about a periphery of the drive gear engageable by a gear of a motor assembly.

15. An implantable drug infusion device comprising, in combination:
    a bulkhead having a race;
    a pump tube having an inlet and an outlet and being positioned within the race;
    a roller assembly configured to compress the tube against the race at one or more points along the path, the roller assembly including at least one roller, the roller assembly comprising at least two biasing members operably connected to the roller to adjustably bias the roller against the tube, the two biasing members forming an angle; and
    a drive assembly to drive the roller assembly relative to the tube along the path so as to move a liquid through the tube.

16. The implantable drug infusion device of claim 15, wherein at least one of the biasing members comprises a coil spring.

17. The implantable drug infusion device of claim 15, wherein at least one of the biasing members is made from a material selected from the group consisting of cobalt, stainless steel, and nitinol shape memory alloy.

18. The implantable drug infusion device of claim 15, wherein the two biasing members each comprises a coil spring.

19. The implantable drug infusion device of claim 18, wherein the two biasing members are made from a material selected from the group consisting of cobalt, stainless steel, and nitinol shape memory alloy.

20. The implantable drug infusion device of claim 15, further comprising a support plate to secure the roller assembly and drive assembly to the bulkhead.

21. The implantable drug infusion device of claim 15, further comprising a motor assembly, the drive assembly driven by the motor assembly.

22. An implantable drug infusion device comprising, in combination:
    a bulkhead having a race, a first chamber, and a second chamber;
    a pump tube having an inlet and an outlet and being positioned within the race, the race configured to support the tube along a path;
    a motor assembly positioned within the first chamber; and
    a pumphead assembly positioned within the second chamber, the motor assembly driving the pumphead assembly, the pumphead assembly comprising a roller assembly having a hub, three roller housings, each roller housing having a roller and being pivotally connected to the hub;

a drive assembly to drive the roller assembly relative to the tube along the path so that the rollers compress the tube to move a liquid through the tube;

the rollers and race defining a gap; and at least two springs operably connected to each roller housing to bias a corresponding roller against the tube, the two springs forming an angle.

23. The implantable drug infusion device of claim 22, wherein the pumphead assembly further comprises a support plate secured to the bulkhead.

24. The implantable drug infusion device of claim 22, wherein the race includes an inlet ramp and an outlet ramp, the inlet ramp and outlet ramp each having an arcuate geometry.

25. The implantable drug infusion device of claim 22, wherein the springs are made from a material selected from the group consisting of cobalt, stainless steel, and nitinol shape memory alloy.

26. An implantable drug infusion device comprising, in combination:

a pump tube for holding a liquid to be pumped;

a race configured to support the tube along a path;

a roller assembly configured to compress the tube against the race at one or more points along the path, the roller assembly including at least two rollers and a hub, the roller operably connected to at least one adjacent roller by a biasing member to bias the roller against the tube, wherein the roller, the adjacent roller and the hub form a triangle, and a drive assembly to drive the roller assembly relative to the tube along the path to move the liquid through the tube.

27. The implantable drug infusion device of claim 26, wherein the roller is operably connected to a first adjacent roller by a first biasing member, and the roller is operably connected to a second adjacent roller by a second biasing member.

28. The implantable drug infusion device of claim 27, wherein the first and second adjacent rollers are operably connected by a third biasing member.

29. The implantable drug infusion device of claim 26, wherein the biasing member is a coil spring.

30. The implantable drug infusion device of claim 26, wherein the biasing member is made from a material selected from the group consisting of cobalt, stainless steel, and nitinol shape memory alloy.

31. The implantable drug infusion device of claim 26, wherein the drive assembly comprises a drive shaft, and a drive gear, the drive gear configured to be rotatably driven by a motor, the drive shaft rotatably driven by the drive gear and rotatably driving the roller assembly.

32. The implantable drug infusion device of claim 31, wherein the drive gear includes a plurality of teeth about a periphery of the drive gear to engage a gear of a motor assembly.

33. The implantable drug infusion device of claim 26, further comprising a bulkhead and a support plate to secure the roller assembly and drive assembly to the bulkhead.

34. An implantable drug infusion device comprising, in combination:

a pump tube for holding a liquid to be pumped;

a race configured to support the tube along a path, the race having a center;

a roller assembly configured to compress the tube against the race at one or more points along the path, the roller assembly including at least two rollers and a hub, the hub having a center, each roller operably and pivotally connected to the hub by a corresponding retracting roller arm and a corresponding biasing member to bias each roller against the tube, wherein the rollers and the hub form a triangle, each corresponding retracting roller arm and corresponding biasing member forming an angle, each roller located at one end of its corresponding retracting roller arm, a drive assembly to drive the roller assembly relative to the tube along the path to move the liquid through the tube, the center of the hub substantially coinciding with the center of the race, the load of the rollers on the tube being substantially uniform.

35. The implantable drug infusion device of claim 34, wherein the biasing member is a coil spring.

36. The implantable drug infusion device of claim 34, wherein the biasing member is made from a material selected from the group consisting of cobalt, stainless steel, and nitinol shape memory alloy.

37. The implantable drug infusion device of claim 34, wherein the roller arm assembly comprises three rollers and corresponding retracting roller arms and biasing members to bias each roller against the tube.

38. The implantable drug infusion device of claim 34, wherein the drive assembly comprises a drive shaft, and a drive gear, the drive gear configured to be rotatably driven by a motor, the drive shaft rotatably driven by the drive gear and rotatably driving the roller assembly.

39. The implantable drug infusion device of claim 38, wherein the drive gear includes a plurality of teeth about a periphery of the drive gear to engage a gear of a motor assembly.

40. The implantable drug infusion device of claim 34, further comprising a bulkhead and a support plate to secure the roller assembly and drive assembly to the bulkhead.

* * * * *